March 25, 1947. F. MEILLAND Plant Pat. 731
ROSE PLANT
Filed Jan. 25, 1944
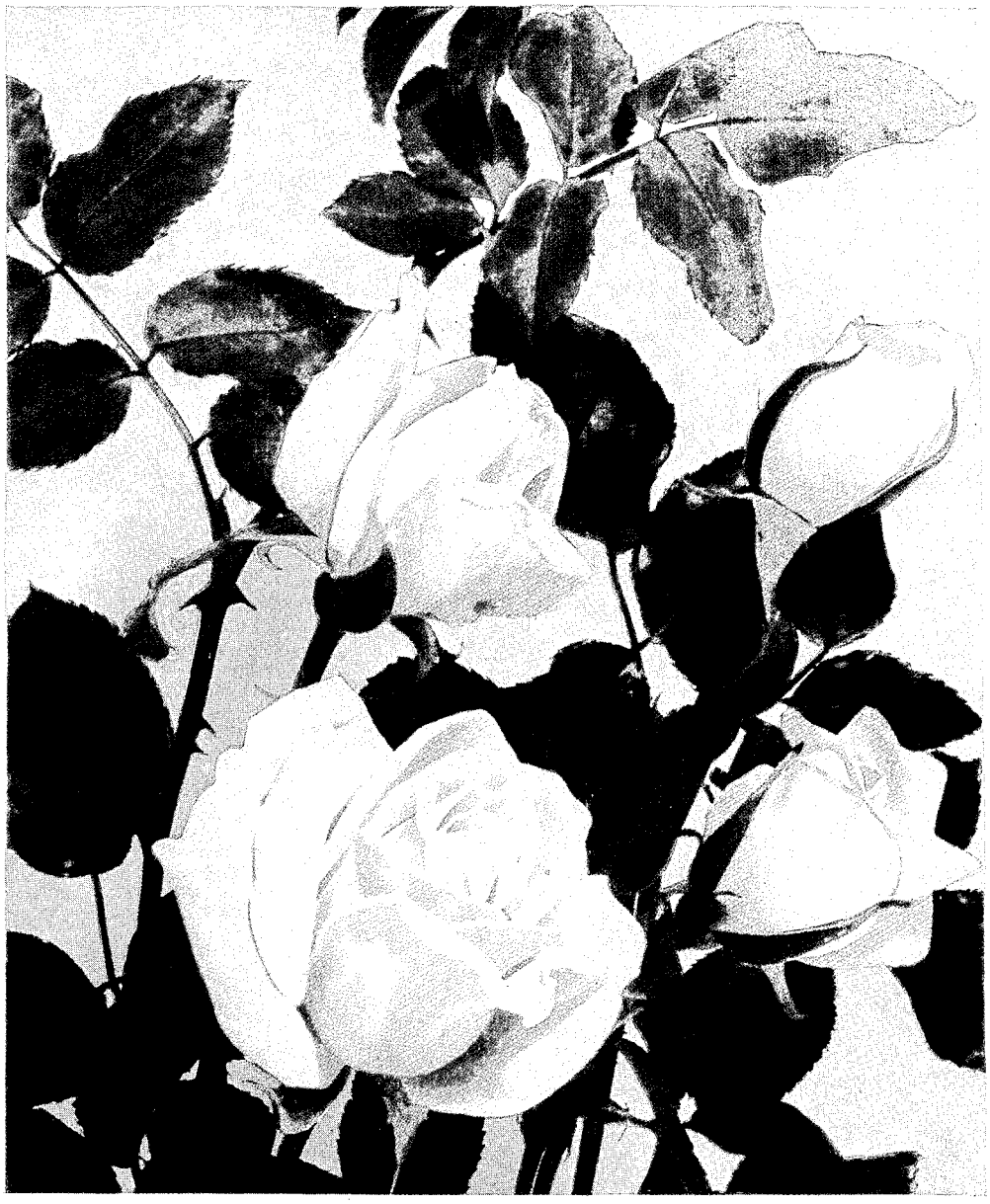
Inventor
Francis Meilland
By Robb & Robb
Attorneys

UNITED STATES PATENT OFFICE

731

ROSE PLANT

Francis Meilland, Tassin-les-Lyon, France, assignor to The Conard-Pyle Company, West Grove, Pa., a corporation of Pennsylvania Application January 25, 1944, Serial No. 519,692

1 Claim. (Cl. 47—61)

The present invention relates to a new and distinct variety of hybrid tea rose plant, particularly useful in outdoor growing not only for garden decoration but also for cut flower purposes.

This new seedling differs from others heretofore existing primarily with respect to its unique coloring, which is hereinafter specifically set forth according to a particular chart of color values, with reference to exemplary specimens grown under control conditions, but tests conducted at various points of the United States disclose that the color may be generally defined as Burnt Orange to Coppery Peach or Apricot, and in this respect resembling the colors of the rose "Orange Nassau." However, the plant of this new variety is far more vigorous and productive than "Orange Nassau." It may be added also that the foliage texture of this variety with its shiny surface is also a distinguishing feature of importance particularly from the standpoint of disease resistance and beauty.

Asexual reproduction of this new variety shows the foregoing characteristics come true to form and are established.

The following is a detail description of the new variety, color terminology being in accord with Ridgeway's Color Standard:

Type: Half hardy; bush; outdoor; seedling; for cut flowers and garden decoration.
Class: Hybrid tea.
Propagation: Holds its distinguishing characteristics through succeeding propagations by budding, which is the only method employed up to the present time.

*Flower*

Locality where grown: West Grove, Pennsylvania.
Flowers borne: Singly; on strong, medium long stems.
Quantity of bloom: Abundant outdoors.
Continuity: Intermittent but almost continuous.
Fragrance: Strong; spicy.
Bud:
*Peduncle.*—Medium long; medium heavy; erect; stiff; Burnt Sienna, Plate II; medium rough; numerous prickles, Mahogany Red, Plate II.
*Before calax breaks.*—Size—large. Form—long pointed with a conspicuous neck; with foliaceous appendages on the surface of of the bud; with bristle-like foliaceous parts extending beyond the tip of the bud equal to three-fourths or more of its length.

*As calyx breaks.* — Color — Ochraceous-Orange, Plate XV.
*As first petal opens.*—Size—large. Form—long; ovoid. Color — outside: Capucine Yellow, Plate III; washed Begonia rose, Plate I; inside: Orange, Plate III.
*Opening.*—Opens up well.
Bloom:
*Size.*—When fully open, large; five inches to five and one-half inches.
*Petalage.*—Double; from 30 to 35 petals; arranged regularly.
*Form.* — High center at first; becoming cupped; petals remaining at first loosely cupped; becoming later, at maturity, loosely rolled outward.
Petals: Thick; with inside shiny-satiny, and outside satiny.
*Shape.*—Outside—obovate, with apex flat; intermediate—obovate; inside—obovate.

This description of a newly opened flower was made from a rose grown outdoors, in the month of October, 1943, at West Grove, Pennsylvania:

*Color.* — *Outside petal* — outside surface: Orange-Buff, Plate III; inside surface: Mikado Orange, Plate III. *Intermediate petal*—outside surface: Light Orange-Yellow, Plate III; inside surface: Cadmium Orange, Plate III. *Inner petal*—outside surface: Light Orange-Yellow, Plate III; inside surface: Cadmium Orange, Plate III.

This description was made from a rose that was open for three days outdoors, in the month of October, 1943, at West Grove, Pennsylvania:

*Outside petal.*—Outside surface: Light Orange-Yellow, Plate III; inside surface: Mikado Orange, Plate III.
*Inside petal.*—Outside surface: Light Orange-Yellow, Plate III; inside surface: Cadmium Orange, Plate III.
*General color effect.*—Newly opened flower—Cadmium Orange, Plate III. Three days open—Mikado Orange, Plate III.
*Behavior.*—Drop off cleanly.
*Flower longevity.*—On bush in garden—3 to 4 days in October. Cut roses grown outdoors kept at living-room temperatures, 3 to 5 days.

*Reproductive organs*

Stamens: Many, arranged irregularly.
Filaments: Medium long; Brazil Red, Plate I; most with anthers.

Anthers: Large; Cadmium Yellow, Plate III.
Pollen: Abundant; Xanthine Orange, Plate III.
Pistils: Many.
Styles: Long; very thin; bunched.
Stigma: Raw Sienna, Plate III.
Ovaries: Enclosed in calyx.
Hips: Short; gourd-shaped; Biscay Green, Plate XVII; smooth; walls thick, fleshy.
Sepals: Long; spear-shaped; recurved with appendages.
Seeds: Few; medium size.

*Plant*

Foliage:

*Leaves.*—Compound of five to seven leaflets; normal abundance; large; heavy; leathery; glossy; wrinkled.

*Leaflets.*—Shape—ovoid with apex acute. Base—Round. Margin—serrate.

*Color.*—Mature—upper surface—Elm Green, Plate XVII; under surface—Light Hellegore Green, Plate XVII. Young—upper surface: Elm Green, Plate XVII; under surface: Roman Green, Plate XVI.

*Rachis (the supporting stem of the compound leaf).*—Heavy. Upper side: smooth; grooved; under side: Sparsely thorny.

*Stipules.*—Medium long; moderately wide; with medium long points, turning out at an angle of more than 45°, recurved toward the stem.

*Disease.*—Resistant to mildew and blackspot insofar as this is evidenced by absence of any throughout development and establishing of this variety.

Growth:

*Habit.*—Bushy; much branched.

*Growth.*—Moderate.

*Canes.*—Heavy.

*Main stems.*—Light Elm Green, Plate XVII. *Thorns*—several; short; hooked downward; with broad base. *Prickles*—None. *Hairs*—None.

*Branches.*—Light Elm Green, Plate XVII. *Thorns*—few; short; hooked downward; with broad base. *Prickles*—none. *Hairs*—none.

*New shoots.*—Claret Brown, Plate I. *Thorns*—many; medium long; hooked downward; with broad base. *Prickles*—none. *Hairs*—none.

I claim:

A new and distinct variety of rose plant, characterized as to novelty by its vigorous habits of growth and productivity, shiny foliage and disease resistance, and unique coloring of its flowers, substantially as shown and described.

FRANCIS MEILLAND.